United States Patent [19]
Webb et al.

[11] Patent Number: 5,321,149
[45] Date of Patent: * Jun. 14, 1994

[54] PROCESS FOR STABILIZING SPENT SILICON CONTACT MASS

[75] Inventors: Steven W. Webb, Clifton Park; Alan Ritzer, Sand Lake; John D. Neely, Clifton Park, all of N.Y.

[73] Assignee: General Electric Company, Schenectady, N.Y.

[*] Notice: The portion of the term of this patent subsequent to Aug. 24, 2010 has been disclaimed.

[21] Appl. No.: 987,860

[22] Filed: Dec. 9, 1992

[51] Int. Cl.$^5$ .............................................. C07F 7/16
[52] U.S. Cl. ...................... 556/472; 502/38; 502/41
[58] Field of Search ................ 556/472; 502/38, 41

[56] References Cited

U.S. PATENT DOCUMENTS

| | | | |
|---|---|---|---|
| 4,758,352 | 7/1988 | Feldner et al. | 210/719 |
| 4,960,523 | 10/1990 | Degen et al. | 210/721 |
| 5,000,934 | 3/1991 | Marko et al. | 423/335 |
| 5,239,102 | 8/1993 | Webb et al. | 556/472 |

OTHER PUBLICATIONS

The Chemistry of Silicon, E. G. Rochow, Chapter 15 of Comprehensive Inorganic Chemistry, Pergamon Press, Metallic Silicides and Silicon Alloys. p. 1361.

Primary Examiner—Paul F. Shaver
Attorney, Agent, or Firm—William A. Teoli; William H. Pittman

[57] ABSTRACT

A method is provided for passivating spent silicon contact mass by heating the spent silicon contact mass at a temperature in the range of from 200° C. to 800° C. in an oxygen containing atmosphere.

4 Claims, No Drawings

PROCESS FOR STABILIZING SPENT SILICON CONTACT MASS

CROSS REFERENCE TO RELATED APPLICATION

This application relates to copending application 07/987,872, filed Dec. 9, 1992, now U.S. Pat. No. 5,243,061 and assigned to the same assignee as the present invention.

BACKGROUND OF THE INVENTION

The present invention relates to a method for treating spent silicon contact mass generated during the production of organohalosilanes by the direct reaction of organic halide with silicon powder in the presence of a copper catalyst.

Prior to the present invention, the disposition of unused spent silicon contact mass, generated during the production of organohalosilane by the direct reaction between silicon powder and an organic halide, such as aryl chloride or an alkyl halide for example methyl chloride, created a serious management problem for organohalosilane manufacturers. Spent silicon contact mass, for example, upon removal from the reactor can be highly reactive in air and often ignites.

One method for passivating or stabilizing spent silicon contact mass which can have an average particle size in the range of about 1 micron to about 200 microns and at least 2% by weight of copper in the elemental or chemically combined state, is shown by Hosokawa, U.S. Pat. No. 4,724,122. Hosokawa combines the spent silicon powder with water, granulates the resulting mixture, and thereafter mixes and/or coats the resulting granules with an inert inorganic powder. Another passivating technique for spent silicon contact mass is shown by Marko et al., U.S. Pat. No. 5,000,934, which employs a strong base at an elevated temperature to digest the hydrophobic siloxane rich coating on the spent silicon contact mass in order to dislodge the carbon coating which forms around the spent bed particles. An additional procedure for deactivating spent silicon contact mass is shown by Ritzer, et al., U.S. Pat. No. 4,892,694, which involves pelletizing the spent silicon contact mass and the impregnation of the pellets with an organic binder in aqueous carrier to stabilize the spent silicon contact mass to make it safe for transportation and disposal.

Additional processes are provided for the recovery of Rochow Synthesis mixtures derived from sludge vessels, as shown by Offenlegungschrift DE 313 1732AI and U.S. Pat. No. 4,758,351 to Felder et al. Mixtures of silicon rich solids and liquid containing polysilanes are subjected to a heat treatment or hydrolysis. For purposes of the invention, sludge vessel synthesis mixtures having a large proportion of liquid polysilanes are to be distinguished from the previously discussed pyrophoric spent silicon contact masses wherein liquid direct process high-boiling materials are not present as a constituent.

There is shown in copending application Ser. No. 07/867,657, filed Apr. 13, 1992, a method for passivating spent silicon contact mass by heating the spent silicon contact mass at a temperature in the range of about 900° C. to about 1400° C. under an inert atmosphere.

Although various procedures are available in the prior art for deactivating pyrophoric spent silicon contact mass generated during the direct method for making organohalosilanes, salvaging of the silicon and metallic values, such as copper, from the contact mass after the deactivation treatment is often not feasible. Additional procedures are therefore constantly being investigated to provide for safe handling of the spent silicon contact mass as well as the salvaging of the metallic values from the contact mass in a convenient manner.

SUMMARY OF THE INVENTION

The present invention is based on the discovery that spent silicon contact mass can be rendered substantially non-reactive in air by converting highly reactive elemental copper in the contact mass to copper oxide. The contact mass can be heated at a temperature in the range of about 200° C. to about 800° C. in an oxygen containing atmosphere, such as air or steam. To enhance gas-solid contact, agitation of the spent powder is preferably employed. Treatment time can vary depending upon such factors as the temperature used, gas-solid contact time during mixing or stirring, the surface area of the spent contact mass and the weight percent of unreacted or elemental copper initially present in the spent contact mass. It has been found that oxidatively stabilized spent silicon contact mass can then be safely handled and transported in bulk.

STATEMENT OF THE INVENTION

There is provided by the present invention, a process for stabilizing spent silicon contact mass generated during the production of organohalosilanes by the reaction between powdered silicon and organic halide in the presence of a direct method catalyst comprising a copper catalyst, which process comprises heating the spent silicon contact mass at a temperature in the range of about 200° C. to about 800° C. in an oxygen containing atmosphere until the spent silicon contact mass is rendered substantially nonreactive in air at temperatures up to 350° C.

Spent silicon contact mass in accordance with the present invention generally has a surface area of up to about 25 $m^2/g$. The spent silicon contact mass prior to treatment can be very reactive to both oxygen and methylchloride at temperatures exceeding 200° C.

Spent silicon contact mass which can be treated in the practice of the invention include materials shown by Marko et al., U.S. Pat. No. 5,000,934, Hosokawa, U.S. Pat. No. 4,724,122 and Ritzer et al., U.S. Pat. No. 4,892,694 which are incorporated herein by reference.

Prior to treatment, the spent silicon contact mass can be collected in a hopper under an inert atmosphere such as a nitrogen atmosphere. Alternatively, it can be conveyed directly to a thermal treatment or annealing zone shortly after it has been generated under direct process conditions. Suitable means for heating the spent silicon contact mass to an appropriate annealing temperature as previously defined, are for example, a calcining furnace or a rotary kiln. Venting of reaction gases such as surface chlorosilanes during treating also can be effected by the employment of an inert gas, such as nitrogen, or a noble gas, for example, argon. Effective treatment can be effected at temperatures in the range of from about 200° C. to about 800° C. A temperature of 250° C. to 400° C. is preferred. Treating times in the range of from about 0.5 to 3 hours or more can be used depending upon such factors as the temperature employed, method of effecting contact between the spent contact mass and the oxygen containing atmosphere, and the spent powder properties. Spent silicon contact mass has been treated or stabilized in accordance with the practice of the invention when it is non-reactive in air at temperatures up to 350° C. Non-reactive means that the treated spent contact mass can be safely transported or stored. Non-reactive also means that treated spent contact mass can exhibit an oxidative weight increase which does not exceed about 1.0% based on the total weight of treated mass after it has been exposed in air at a temperature maintained at about 400° C. for a period of up to about 15 minutes.

In order that those skilled in the art will be better able to practice the present invention, the following examples are given by way of illustration and not by way of limitation. All parts are by weight.

EXAMPLE 1

Untreated spent silicon contact mass was obtained from a methylchlorosilane reactor. A portion of the untreated spent silicon contact mass was heated in nitrogen at 400° C. and then rapidly exposed to room air. A flame appeared on the surface of the powder. About 0.5 gram of the untreated spent contact mass was slurried in 125 cc of hot caustic (pH 10, 85° C.). A voluminous and stable foam rapidly developed 3-4 inches thick above the slurry. A portion of the spent silicon contact mass was placed in a glass jar and heated to 350° C. in open air. The powder smoked, glowed and the surface became red in color.

About 75 grams of the spent silicon contact mass was contacted with 150 ccm of dry air at 300° C. in a stirred bed reactor. A 90° C. exotherm was observed while the spent contact mass stirred. After about 2 hours, the powder was cooled and collected. When heated in air to 350° C., the powder showed no tendency to smoke or glow. When contacted with hot caustic as described above, a substantial reduction in reactivity was observed. These results show that after it was treated in accordance with the practice of the invention, the spent silicon contact mass was substantially stabilized.

EXAMPLE 2

About 200 mg of the spent contact silicon mass, shown in Example 1, was heated in a tared microbalance under 100 cc per minute of flowing dry air. Total weight uptake after about 15 minutes was 3.1%. The resulting powder showed no tendency to burn when reheated in air or when exposed to hot caustic in accordance with the method of example 1.

Various nitrogen-oxygen mixtures having about 3.5 to 21% by weight of oxygen were used to stabilize the spent silicon contact mass at temperatures between 400°-500° C. The oxygen-uptake and maximum oxygen uptake rate were measured using a microbalance to determine weight change in the heated samples. The results are shown as follows:

TABLE 1

Passivation of Spent Contact Mass by Air Oxidation Using Oxygen - Nitrogen Mixtures

| Wt. % Oxygen | Temperature °C. | Oxygen-Uptake (%) | Maximum $O_2$ Uptake Rate (mg/g/min) |
| --- | --- | --- | --- |
| 21 | 400 | 2.85 | 13 |
| 10 | 400 | 2.74 | 8 |

TABLE 1-continued

Passivation of Spent Contact Mass by Air Oxidation Using Oxygen - Nitrogen Mixtures

| Wt. % Oxygen | Temperature °C. | Oxygen-Uptake (%) | Maximum $O_2$ Uptake Rate (mg/g/min) |
| --- | --- | --- | --- |
| 3.5 | 400 | 2.68 | 6 |
| 3.5 | 500 | 3.5 | 6.5 |

When the above samples were further heated under the above conditions, the incremental oxygen-uptake was less than 0.1%. These results showed that passivation of the samples had taken place.

EXAMPLE 3

A series of runs were made using 150 gram samples of spent contact mass as shown in example 1, which were placed in a 1 L stirred vessel. Mixtures of steam at 15 psig and nitrogen were passed at roughly 500 cc per minute over the samples. The powders were heated to 300° C. using different steam/nitrogen ratios. Contact with the steam mixtures lasted about 2 hours. The samples were cooled in dry nitrogen, collected and analyzed for pyrophoricity by the tests described in Example 1. The final steam treated powders did not smoke or glow when heated in air to 350° C. The powders were then evaluated in accordance with the procedure of example 2 for weight uptake due to oxidation in air at temperatures up to 400° C. Table 2 shows the results of the weight uptake determination due to steam oxidation at varying steam concentrations measured in Relative Humidity (RH).

TABLE 2

Oxygen uptake in a Microbalance on Air to 400° C. for Steam-Treated Spent Contact Mass at 2 different Steam Concentrations (RH)

| Relative Humidity | Oxygen Uptake (%) |
| --- | --- |
| 27 | 1.1 |
| 2.7 | 0.68 |

The above results show that the spent contact masses can be stabilized at the various RH conditions described above.

Although the above examples are directed to only a few of the very many variables which can be employed in the practice of the method of the present invention, it should be understood that the present invention is directed to a method for treating spent contact mass using a much broader variety of oxidation conditions as shown in the description preceding these examples.

What is claimed is:

1. A process for stabilizing spent silicon contact mass generated during the production of organohalosilanes by the reaction between powdered silicon and organic halide in the presence of a direct method catalyst comprising a copper catalyst, which process comprises heating the spent silicon contact mass at a temperature in the range of about 200° C. to about 800° C. in an oxygen containing atmosphere until the spent silicon contact mass is rendered substantially non-reactive in air at temperatures up to 350° C.

2. A process in accordance with claim 1, where the spent silicon contact mass is generated during the production of methylchlorosilane.

3. A process for treating spent silicon contact mass in accordance with claim 1, where the contact mass is exposed to air during the heating step.

4. A process for treating spent silicon contact mass where the spent contact mass is exposed to steam during the treating step.

* * * * *